United States Patent
Wallstén et al.

(10) Patent No.: US 6,302,904 B1
(45) Date of Patent: Oct. 16, 2001

(54) DEVICE AND METHOD FOR MEDICAL TREATMENT

(75) Inventors: Hans I. Wallstén, Denens; Michel Bachmann, Vaux s/ Morges, both of (CH); Pär Henriksson, Lund (SE)

(73) Assignee: Wallsten Medical S.A., Denens (CH)

( * ) Notice: Subject to any disclaimer, the term of this patent is extended or adjusted under 35 U.S.C. 154(b) by 0 days.

(21) Appl. No.: 09/461,053

(22) Filed: Dec. 15, 1999

(30) Foreign Application Priority Data

Dec. 17, 1998 (SE) ..................................... 9804388

(51) Int. Cl.$^7$ ....................................................... A61F 7/00
(52) U.S. Cl. .......................... 607/105; 607/113; 607/138; 607/98
(58) Field of Search .................. 607/96, 98, 99, 607/101, 102, 104, 105, 113, 114, 138; 606/191–194; 604/96.01–100.03

(56) References Cited

U.S. PATENT DOCUMENTS

| | | |
|---|---|---|
| 4,016,867 * | 4/1977 | King et al. . |
| 4,949,718 | 8/1990 | Neuwirth et al. . |
| 5,084,044 | 1/1992 | Quint . |
| 5,449,380 * | 9/1995 | Chin ...................... 607/105 |
| 5,514,093 | 5/1996 | Ellis et al. . |
| 5,676,654 | 10/1997 | Ellis et al. . |
| 5,693,080 | 12/1997 | Wallstén et al. . |
| 5,776,129 * | 7/1998 | Mersch .................. 606/31 |
| 5,800,493 * | 9/1998 | Stevens et al. ......... 607/113 |
| 6,139,570 * | 10/2000 | Saadat et al. .......... 607/105 |

FOREIGN PATENT DOCUMENTS

| | | |
|---|---|---|
| 4224595 | 1/1994 | (DE) . |
| 9404021-9 | 12/1998 | (SE) . |
| WO94/21202 | 9/1994 | (WO) . |
| WO96/26695 | 9/1996 | (WO) . |

* cited by examiner

Primary Examiner—Roy Gibson
(74) Attorney, Agent, or Firm—Burns, Doane, Swecker & Mathis, L.L.P.

(57) ABSTRACT

A device for carrying out hyperthermia in a mammalin uterus cavity, including an elongate, rigid distal section (3) and a flexible and elastic bladder (9) encompassing said distal section which, together with said bladder, is intended for insertion into said uterus cavity, further including means (27) for the supply of a heat-transmitting medium under pressure for the expansion of said bladder (9) within said uterus cavity, and heating means (29) for heating said medium, the device further having an intermediate section (5) whose distal part when inserted is positioned in a cervix canal belonging to said uterus, and a proximal section (7) for operating the device, said distal and intermediate sections (3,5) containing at least a central tube (17), whose distal part is surrounded by said bladder and is provided with at least one outlet (19) for said medium within said bladder, and whose intermediate part is surrounded by an axially displacable tube (21;35), onto whose distal end (23;51) the proximal end (25) of said bladder (9) is attached, characterized by means (15;45) for determining the axial position of the distal end (23;51) of said axially displacable tube and thereby also the axial position of the proximal end (25) of said bladder (9) so that the length of said bladder (9) matches the depth of a cavity subject to treatment, and means (13;47) for locking said tube (21;35) with its distal end (25;51) in such matching position; and the invention also involves methods of thermal treatment of human uterus cavity linings and a device for thermal treatment of mammalian body cavities or ducts, such as urethras.

28 Claims, 3 Drawing Sheets

DEVICE AND METHOD FOR MEDICAL TREATMENT

FIELD OF THE INVENTION

The present invention relates to a device for thermal treatment of a mammalian body cavity or duct, such as for carrying out hyperthermia in a mammalian uterus cavity or a urethra, and to methods for such treatment.

BACKGROUND ART

In the treatment of certain disorders occurring in body cavities or ducts frequently heat is supplied, so called hyperthermia. It has for example been known for a long time that so called menorrhagia, i.e. a disorderly condition, characterized by strong menstrual bleeding, can be cured by heat destruction of the so called endometrium, which is a mucosal membrane lining the uterus cavity. Said cavity has in a front view a triangular shape with a base facing upward. The cervix canal opens in the lower triangle apex and the fallopian tubes in the upper, counter-positioned triangle apexes.

Since access to the cavity can take place only through the cervical canal which is narrow it has inter alia been suggested to use catheters having an expandable bladder connected to the distal end of the catheter. When treating menorrhagia the front end of the catheter comprising the unexpanded bladder is inserted into the uterus cavity via vagina and cervix.

The bladder is then expanded by means of the supply of a pressure medium, for example a liquid, via a canal centrally placed in the catheter from a liquid container, whereby the usually rather flat cavity is widened so that the balloon will engage the major part of the surface of the endometrium. Clinical tests have shown that it is important for a successful result of the treatment that the entire endometrium is heated with the exception of the cervical area and that the pressure is maintained at a relatively high level, suitably up to 160–200 mm Hg, so as to improve heat convection, partly in view of the fact that the circulation of blood in the tissue will be reduced. On the other hand the pressure should not exceed about 250–300 mm Hg in view of risk of rupture of the tissue.

The pressure medium is then heated by heat-releasing means, for example an electric resistance element, to a suitable temperature, for example between 70 and 90° C. When the temperature has been reached the treatment starts and is directed to necrotizing the endometrium under heat and pressure to a depth of about 5–7 mm. Normally, a period of treatment of between 6 and 15 minutes is sufficient.

Expandable balloon catheters for the heat treatment of menorrhagia are described for example in U.S. Pat. No. 4,949,718 (Neuwirth et al), U.S. Pat. No. 5,693,080 (Wallsten), WO94/21202 (Wallsten et al), WO96/26695 (Claren et al), U.S. Pat. No. 5,084,044 (Quint).

Since the cervical canal normally has a diameter of only 3–5 mm the treatment must as a rule be preceded by dilatation with a so called Hegar dilator in order to allow for passage of the balloon catheter. The dilatation is painful and the degree of pain is often related to the extent of dilatation. For certain catheters appearing on the market a dilatation to 8–9 mm must be made which increases the requirement for anaesthesia.

Therefore, it is highly desirable to design such catheters with a small diameter in order to reduce the degree of dilatation and to facilitate insertion. On the other hand the cervical canal is sensitive to the effect of heat. Heating can result in the formation of stenosis completely obstructing the canal. Therefore, the canal has to be protected by heat insulation surrounding the canal. Since the efficiency of the heat insulation is largely dependent on the radial thickness thereof one has to compromise between the wish for a small catheter diameter and an efficient heat insulation.

In U.S. Pat. No. 4,949,718 and U.S. Pat. No. 5,693,080 balloon catheters are described where the heat-releasing means is centrally positioned in the balloon. In the first case it is constituted by an electric resistance coil and in the other case a non-linear electric resistance of so called PTC type.

In the latter case forced circulation is generated within the balloon by exerting pulsation on the heating medium in the inlet passage, whereas no circulation is used in the device according to U.S. Pat. No. 4,949,718. In the devices described in WO94/21202, WO96/26695 and U.S. Pat. No. 5,084,044 the liquid is circulated through an inlet passage and an outlet passage between the balloon and an external heat source.

Generally, one can say that devices using a circulating liquid result in an effective and even heat transfer and thereby good result of treatment. On the other hand it is important that the expanded balloon is adapted to the cavity surface to be treated. Such devices also require efficient insulation in the cervical area in view of the large amount of hot liquid that circulates through the supply and discharge conduits.

The size of the uterus cavity varies greatly between different patients. The length or depth of the cavity is usually between about 40 mm and 80 mm and the length of the cervical canal varies between about 20 and 40 mm. The cavity volume as extended by a balloon or bladder is between about 3 and 60 ml.

A problem associated with devices for heat destruction of the endometrium using balloon catheters is the large variation of volumes and cavity depths. As previously indicated it is important that the balloon or bladder engages the major part of the endometrium surface and that it can be expanded outwardly towards the fallopian corners. On the other hand the cervical canal and its opening into the cavity, the so called istmus region, must be protected from influence by heat.

This problem has been solved in said U.S. Pat. No. 4,949,718 in that the catheter has a scale graduation by which a suitable insertion depth can be selected. Since the proximal end of the bladder is attached to the distal end of the catheter, whereas the distal end of the bladder is free, the balloon will move axially forward when expanded so as to be brought into contact with the endometrium (FIGS. 1, 2, 7 and claim 1). The intention is that the operator choses the insertion depth so that the attachment of the bladder to the catheter is forward of the cervix so as to prevent all contact between the bladder and the cervical canal.

This device is associated with several drawbacks. Since the distal end of the catheter moves freely somewhere in the middle of the cavity, and since the balloon or bladder when expanded exerts a certain counter pressure, it is difficult for the operator to check the correct position, whereby there is risk for heat damages on the cervix. Furthermore, there is risk that the catheter points obliquely so as to perforate the cavity wall or so as to cause burn damage in view of contact between the hot resistance element and the wall. Another disadvantage is that the proximal part of the balloon also can expand axially rearwardly causing risk for heat damage at the opening of the cervical canal into the cavity.

In the devices according to the other references the balloon is attached to the cavity both in its proximal and in its distal part. When inserted the catheter is moved so as to reach the cavity fundus. In view of the fact that the catheter is attached at both ends thereof it will in its expansion automatically be centered to the center of the cavity.

The balloons of the device according to WO94/21202 are constituted by for example pre-shaped balloons. The pre-shaped balloons or bladders are designed with the wide part placed distally. Such balloons are, accordingly, adapted to the shape of the cavity and would have the advantage that they will have a better reach when expanded out into the fallopian corners. The pre-shaped balloons are folded around the catheter before insertion, which is a disadvantage in view of a increase of the diameter.

In a particular embodiment the pre-shaped balloon ban be axially stretched so that the diameter will be reduced and insertion facilitated. After the insertion of the catheter the balloon is reverted to its original position so that it can completely fill the uterus cavity.

In WO96/26695 there is described a balloon catheter which is connected to an external heat source and where the liquid is circulated between the balloon and an external liquid container via passages or canals. The catheter is constituted by a tube which is closed at its distal end. The distal section of the tube is surrounded by an elastic piece of hose of silicon rubber which in an unexpanded state adheres to the exterior surface of the tube and is attached to the tube at both ends thereof. With supply of liquid the hose piece will be extended to a balloon.

A sleeve is arranged around the catheter tube and is axially displacable thereon. Near its distal end the sleeve has an exterior shoulder. With retracted sleeve the catheter is inserted and the sleeve is then pushed forward until engaging the cavity entrance, the so called sound measure constituted by the sum of the cavity depth and the cervical canal length can be determined from a scale. The expandable part of the hose piece, i.e. the length of the balloon, can thus be adapted to the cavity depth of the uterus.

However, this device is associated with several disadvantages. As a balloon material there can only be used a tubular piece so as to enable displacement of the sleeve. Furthermore, the displacable sleeve with the necessary play between the sleeve and the catheter tube results in a considerable increase of the diameter of the catheter which, as previously indicated, is not desirable. From the description of said patent application it is not clear how the necessary heat insulation of the catheter part positioned in the cervical canal is arranged. It is, however, obvious, that in view of the necessary gap or play blood and body liquid can enter and impair the insulation.

A further disadvantage is that the length of the balloon according to this device is determined by the sound measure. Since the latter can also vary from individual to individual as introductorily mentioned the length of the balloon will not always match the cavity depth.

Except for WO96/26695 all devices mentioned above contain no means for adjusting the balloon length to match different cavity depths.

OBJECTS AND SUMMARY OF THE INVENTION

The present invention has for an object to provide hyperthermia for the treatment of disorders in the uterus cavity by means of a balloon catheter designed in such a manner that the active length, i.e. the heat emitting length of the balloon can be adjusted before the heat treatment to match the depth of a cavity subject to treatment and locked in such position.

Another object of the invention is to enable variation of said balloon length to match cavity depths within the range about 3 to about 10 cm corresponding to the minimum and maximum cavity depths, respectively, without substantial influence on the so called plateau pressure of the balloon.

Yet another object of the invention is to provide a catheter of small diameter of the section to be introduced through the cervical canal.

A further object of the invention is to provide a balloon catheter, the balloon material of which is highly elastic allowing the balloon when mounted onto the catheter tube to be pre-stretched also in the position corresponding to a small cavity depth in order to stabilize the shape of the expanded balloon.

Still another object of the invention is to provide a balloon catheter using a pre-formed balloon of a highly elastic material in the shape of a cone, the balloon being pre-stretched at the mounting operation so that in the position corresponding to the minimum cavity depth the balloon takes a substantially cylindric shape for the purpose of facilitating insertion and removal of the catheter.

Another object of the invention is to provide a balloon catheter consisting of a few parts for ease of mass production, said parts being easy to assemble thereby allowing low production costs.

Yet another object of the invention is to provide a balloon catheter designed to enable removal of gases, especially air, contained in the catheter in a simple manner in connection with filling the catheter with heating medium in preparation for treatment.

A further object of the invention is to provide a balloon catheter having means for measuring the pressure inside the balloon, said means better reflecting the true pressure inside the balloon.

In development work leading to the present invention it was unexpectedly found that the degree of radial expansion was substantially independent of the degree of axial stretch of the bladder. Moreover, the axial stretch of the bladder was not seen to have any influence on the so called plateau pressure. These surprising findings have enabled a high degree of operational flexibility in regard to adapting the catheter to uteri of varying depths and shapes.

The above and other objects will be apparent from the following description embracing a summarizing part of the invention and description of specific embodiments thereof.

The device for carrying out hyperthermia in a mammalian uterus cavity, more particularly a human uterus cavity, comprises an elongate, rigid distal section and a flexible and elastic bladder encompassing said distal section. Said section together with the bladder is intended for insertion into a uterus cavity subject to treatment. The device further comprises means for the supply of a heat transmitting medium under pressure for the expansion of said bladder within the uterus cavity, and heating means for heating said medium. The device further comprises an intermediate section whose distal part when inserted is positioned in a cervix canal associated with the uterus subject to treatment, and a proximal section for operating the device. The distal and intermediate sections contain at least a central tube the distal part of which is surrounded by said bladder and is provided with at least one outlet for the medium to enter said bladder. Its intermediate part is surrounded by an axially displacable tube, onto whose distal end the proximal end of the bladder is attached. The device according to the invention contains for its proper function means for determining the axial position of the distal end of the axially displacable tube and thereby also the axial position of the proximal end of the bladder, so that the heat-emitting length of the bladder will match the depth of the cavity subject to treatment. For such a function the device also contains means for locking the axially displacable tube with its distal end in such matching position.

The axially displacable tube is suitably displacable between a first position matching a minimal cavity depth and a second position matching a maximal cavity depth. It is preferred that the distance corresponding to said minimal depth results in a pre-stretched position of the bladder.

The device according to the invention comprises, according to one aspect of the invention, means generating internal circulation through said bladder. The heating means may be comprised by heating element placed within the bladder or a heating element placed within the proximal section of the device.

Suitable heating elements are selected from elements of the type based on electric resistance heating, microwaves, laser and autocontrol. An element of the autocontrol type preferably contains PTC or Curie point materials.

For evacuation of air when filling the system the device according to the invention may be provided with a valve arranged at the distal end of the central tube. It is preferred for proper orientation of the distal end of the central tube that it is attached to the distal wall of the bladder.

In a particularly preferred embodiment of the invention the device is provided with an inlet passage for introducing medium into the bladder and an outlet passage for said medium. Said outlet passage can enable evacuation of air from the system in connection with such introduction of medium.

For providing efficient heat transfer to the uterus lining the device according to the invention may contain a pulsating pressure means placed in the inlet passage and counteracting back valves positioned between such pulsating means and the bladder. In this arrangement one of the valves is arranged to open the inlet passage on a positive pulse, whereas the other valve opens a connection between the outlet passage and the inlet passage on a negative pulse. By such arrangement circulation of the medium through the bladder will be provided.

According to one embodiment of the invention a pressure means may be connected to the outlet passage for measuring pressure inside the bladder during treatment.

In a particularly preferred embodiment of the present invention the device contains an intermediate tube concentric with and surrounding the central tube. Such intermediate tube is at its distal end connected to the axially displacable tube so that it can move as a unit together with said axially displacable tube. In this manner the distal part of the outlet passage is formed by a gap defined between the central tube and the surrounding intermediate tube.

In order to protect the cervical canal and in particular the cervix from excessive heating the axially displacable tube surrounds the central tube or the intermediate tube with the formation of an annular gap acting as a thermal insulation. Said gap may either be filled with a gas, especially air, or with a porous material providing efficient heat insulation.

The invention also provides a method for thermal treatment of a human uterus cavity lining, said method comprising the steps:

a) estimating the depth of said cavity;

b) adjusting and securing the distance between the axial ends of the heat-emitting part of an elastic bladder to match said cavity depth;

c) inserting the bladder prepared as per step b) above into said cavity;

d) inflating said bladder by introducing a fluid therein under pressure to bring said bladder into contact with substantially all of said lining;

e) heating said fluid to a treatment temperature and maintaining said temperature for a period of time resulting in necrosis of substantially all of said lining; and f) removing said fluid from said bladder and withdrawing the latter in a collapsed state from said cavity.

As an alternative to the method according to the invention as outlined above steps b) and c) can be reversed in that the adjusting and securing of the distance between the axial ends of the heat-emitting part of the bladder to match said cavity depth follows step a), whereas insertion of the axially extended bladder into the cavity subject to treatment takes place subsequent to the adjustment and securing step.

In this disclosure the expressions "distal" and "proximal" are used with the meaning "front" and "rear", respectively, i.e. related to the operator of the instrument or device.

DETAILED DESCRIPTION OF THE INVENTION

The invention will in the following be further described by exemplifying embodiments which, however, must not be construed to restrict the scope of protection except as defined in the appended claims. These embodiments are described with reference to the appended drawings, wherein:

Figure 1:
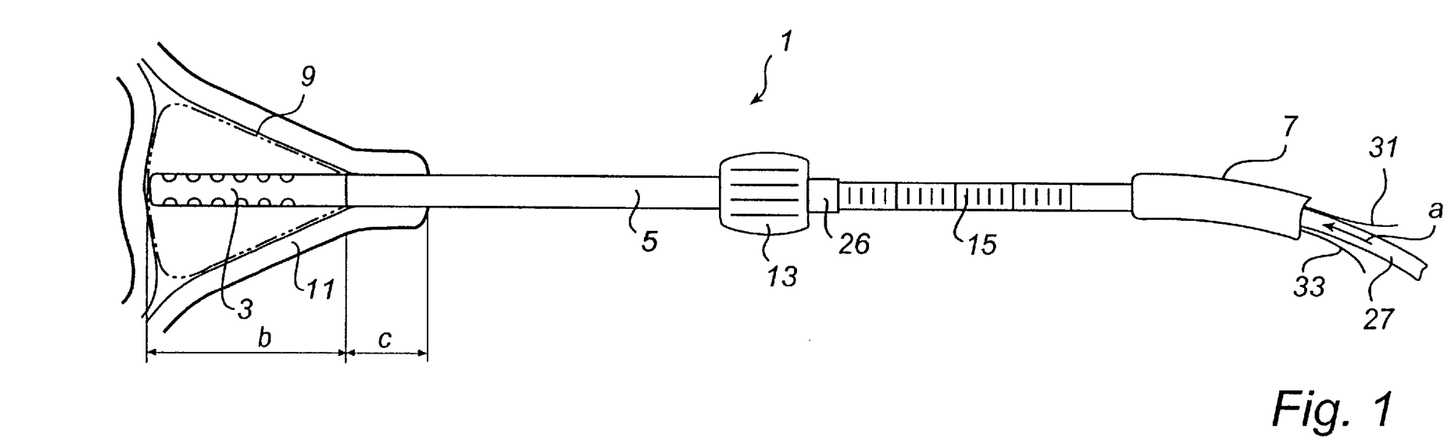
FIG. 1 is a simplified diagrammatic illustration of a device according to the present invention.

FIG. 1 shows in a simplified manner a sideview of a device designed in accordance with the present invention. To the left in FIG. 1 there is diagrammatically shown a human uterus 11 into which the distal section 3 of the device generally indicated 1 has been inserted. After the insertion a bladder 9 has been brought to expand inside the uterus cavity as shown by point-dashed lines in FIG. 1.

The device shown further comprises an intermediate section 5, a proximal section 7, a scale 15 to be used when adjusting the heat-emitting length of the balloon 9 to the cavity depth, and a locking nut 13 for securing or maintaining this position.

Figure 2:
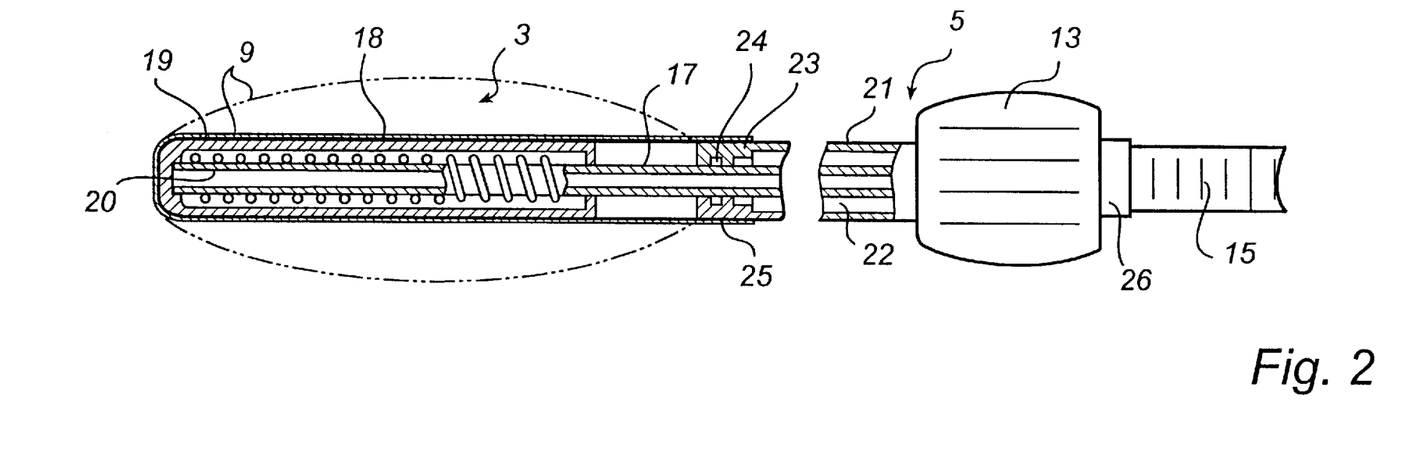
FIG. 2 is an enlarged diagrammatic illustration partly in section of part of the device shown in FIG. 1.

FIG. 2 shows more in detail the distal and intermediate sections 3,5 of the device shown in FIG. 1. Extending through said two sections 3,5 is a central tube 17. At its distal part central tube 17 carries a resistance heating element indicated as a coil 29, and said heating element is in turn surrounded by a housing 18 attached to the central tube 17 at both ends thereof. The central tube 17 and the housing 18 are provided with radial holes 19 and 20 for a purpose to be described below.

In the intermediate section 5 the central tube 17 is surrounded by an axially displacable tube 21 which at its distal end 23 sealingly by an O-ring 24 surrounds the central tube 17. An annular space 22 is formed between the axially displacable tube 21 and the central tube 17 and has for its purpose to provide heat insulation. The bladder 9 embraces a distal part of the central tube 17 and the housing 18 and is attached at its distal end to the front end of the device and at its proximal end 25 to the distal end 23 of the axially displacable tube. The bladder 9 is shown by full lines in its unexpanded state closely surrounding the distal end of the device and in a partly expanded state corresponding to its heat-emitting length by point-dashed lines.

When axially moved the displacable tube 21 together with a locking nut 13 moves along the scale 15 which is graduated so that the proximal end 26 of tube 21 can be placed in a position corresponding to the cavity depth. The displacable tube 21 is then locked by turning locking nut 13 to a locking position. Such locking can be made by by an excenter design or by clamping tongues or jaws.

FIG. 1 shows in a diagrammatic manner electric leads 31,33 for the supply of electric current to the heating element 29, for registration temperature or the like. Furthermore, an inlet at arrow a) is indicated by a flexible hose 27 attached to the distal end of central tube 17 for the purpose of introducing a heating medium into the instrument for the expansion of the bladder and heating of the uterus cavity endometrium and for removal of the medium after treatment.

The instrument shown in FIGS. 1 and 2 is based on non-circulation of the heating medium which is introduced at arrow a) through conduit 27 and central tube 17, where it enters the interior of the bladder through openings 19 and 20. When heating the uterus cavity it is important that the heat-emitting length of the bladder is adapted to the cavity depth so that heating of the cervical canal at the proximal end of the bladder is avoided.

The instrument shown in FIGS. 1 and 2 contains the feature of adjusting the balloon length which is made possible by the arrangement with the axially displacable tube 21 having the proximal end of bladder 9 attached to its distal end 23. Before starting treatment the operator or physician measures by the use of a sound the distance composed of the cavity depth b and the length c of the cervical canal as indicated in FIG. 1. This distance b+c is called the probe or sound measure. After estimating the length of the cervical canal and subtracting this length from the sound measure there is obtained a measure b equaling the depth of the cavity. By unlocking nut 13 the displacable tube 21 can now be moved, as defined by the proximal end 26 of said tube 21, to a position along graduated scale 15 corresponding to the estimated cavity depth. The nut 13 is then turned into locking position and the catheter can be inserted into position, the bladder inflated and the treatment can be started. By the adjustment of the heat-emitting length of the balloon undesired heating of the cervical canal can now be avoided.

The advantage of the device shown in FIGS. 1 and 2 is inter alia that the bladder must not necessarily have a straight tubular shape. By moving the displacable tube 21 the bladder material can be axially stretched thereby enabling easy insertion through the cervical canal in preparation for treatment.

When studying the expansion capacity of balloons or bladders the term plateau pressure is of significance. By this is meant the pressure needed to expand the bladder without exterior restriction to a certain volume or a certain diameter. The plateau pressure is inter alia dependent on the elastic properties of the bladder material, the shape of the bladder in expanded state and the wall thickness of the material. When using bladders for the treatment of uterus using heat it is desirable that the plateau pressure is low also during expansion to large volumes. A high plateau pressure would reduce the effect of heat conduction and blood circulation when the bladder is expanded under a pressure of 160 to 200 mm Hg, particularly when treating large uterus volumes.

Figure 3:
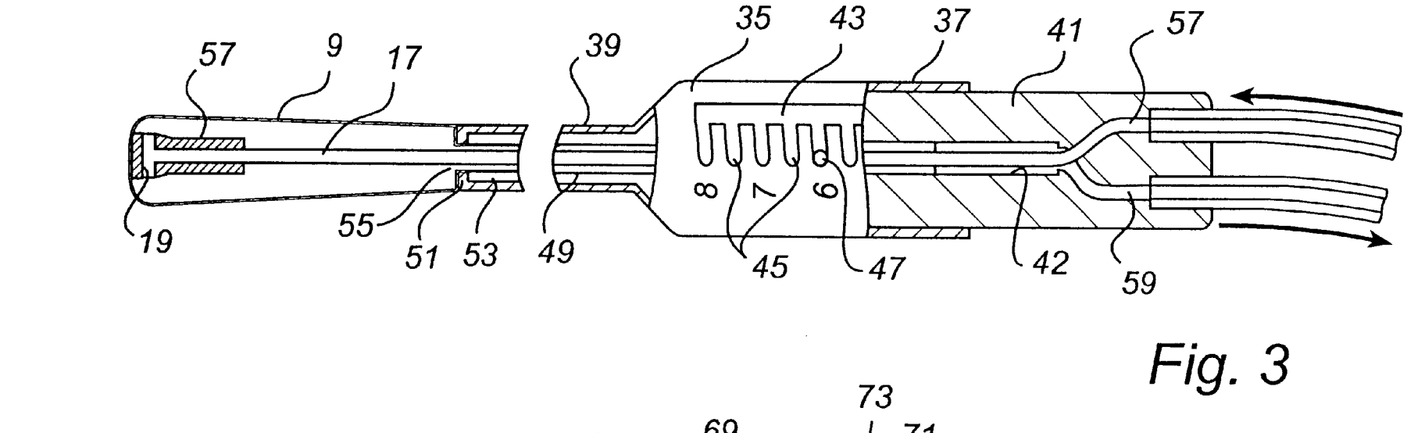
FIG. 3 is a side view partly in section of another embodiment of the device according to the invention.

FIG. 3 shows another embodiment of the device according to the invention. In this embodiment the central tube and the bladder are indicated with the same reference numerals as those used in FIGS. 1 and 2. However, at the front end of the central tube 17 a sleeve 57 is arranged concentric with the tube 17, and the distal end of sleeve 57 is attached to the inside of the bladder 9. Openings 19 provide connection between the interior of the central tube 17 and the interior of bladder 9.

The axially displacable tube 35 is in this embodiment provided with a proximal enlarged part 37 and a distal narrower part 39. The proximal part 37 is slidably arranged on an elongate body 41 containing passages 57 and 59 for the introduction of a heating medium and discharge of the medium, respectively. Concentric to the central tube 17 and the axially displacable tube 35 there is arranged an intermediate tube 49 extending from the distal end of tube 35 and proximally into a bore 42 provided in the elongate body 41. At the distal end thereof the intermediate tube 49 is sealingly attached to an inward flange 51 on the axially displacable tube 35. In this manner tubes 39 and 49 can be axially displaced as a unit for the adaptation of the bladder length as described above. By the concentric arrangement of the intermediate tube 49 around central tube 17 there is provided an outlet passage gap 55 opening providing connection inside the elongate body 41 with the outlet passage 59. Between the intermediate tube and the surrounding axially displacable tube part 39 an insulating annular space 53 is formed acting as a heat insulation to prevent excessive heating of the cervical canal.

The enlarged part 37 of the axially displacable tube 35 is provided with an axially extending slot 43 and connecting side recesses or cut-outs 45 for a purpose to be described. Extending out through a slot 43 or cut-out 45 is a knob or locking element for a purpose also to be described.

By rotating the axially displacable tube 35 the knob 47 can move into the axially extending slot 43 thereby allowing axial displacement of tube 35. After measuring the sound measure as described above the knob 47 can then be positioned in a recess or cut-out 45 matching the cavity depth as measured. Slot 43 and recesses 45 furthermore contribute to ventilation of the air contained in the annular space 53 to further improve the heat insulating efficiency.

In the embodiment shown in FIG. 3 circulation is used in that heated medium is introduced through inlet passage 57 to fill the bladder 9 and to exert pressure on the surrounding cavity lining and also heating thereof and the medium introduced is discharged through outlet passage 59. The heating takes place by external heat exchange in a manner not shown in the drawing. However, the heating system can be of the type for example in WO96/26695, the disclosure of which is incorporated herein by reference.

Figures 4, 6:
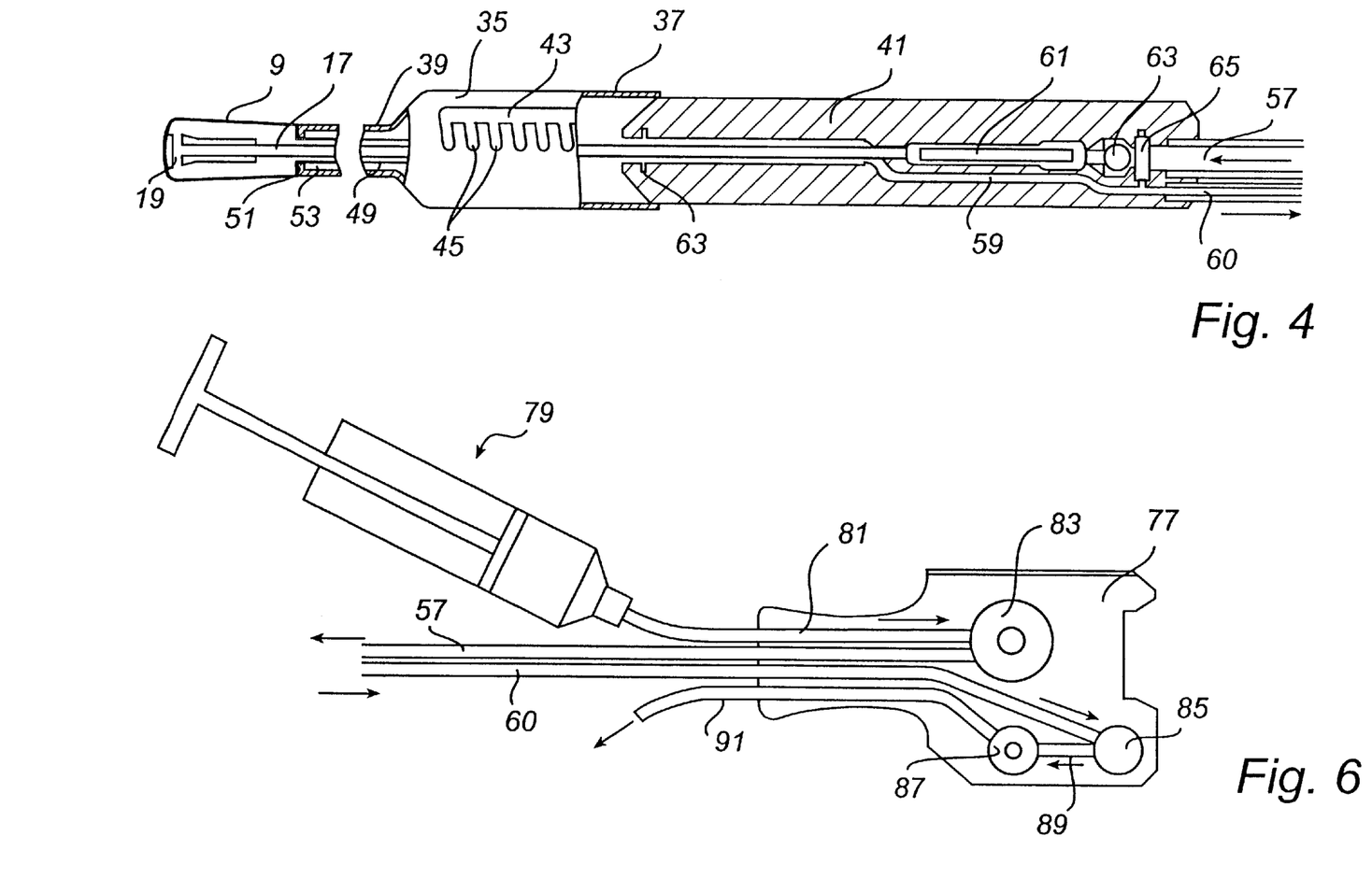
FIG. 4 is a similar view of yet another embodiment of the device according to the invention.
FIG. 6 illustrates a detail of the device involving the system for introducing heating medium and for connection to a central unit for the operation of the device.
Figure 5:
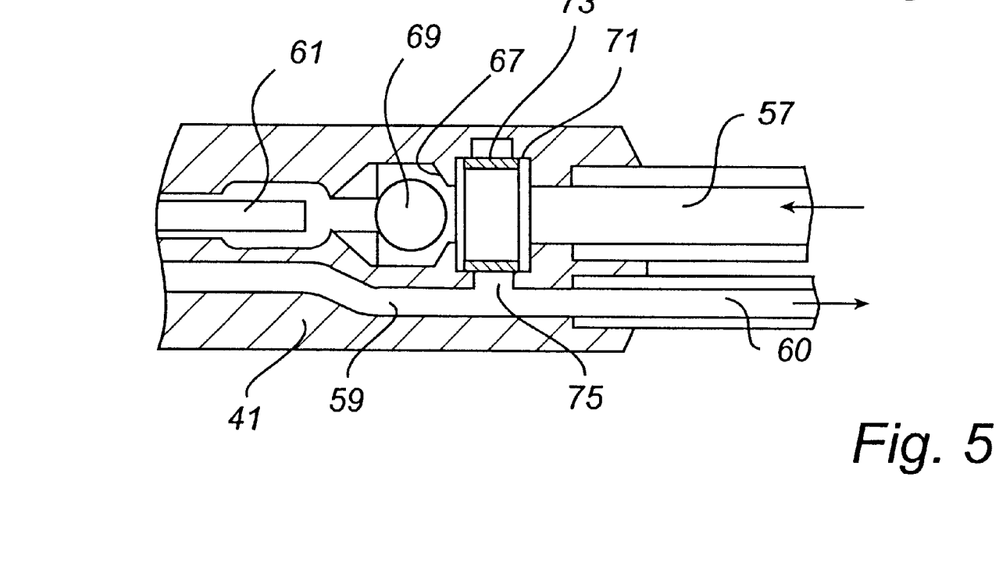
FIG. 5 is an enlarged section of a detail of the device shown in FIG. 4.

In FIGS. 4 and 5 there is described an embodiment similar to that shown in FIG. 3 but wherein the heating element and an arrangement of valves are arranged inside the elongate body 41. As is seen in FIG. 4 a heating element is located inside body 41 in the inlet passage 57, and said element 61 can be of any type as described earlier. The valve system is further illustrated by an enlarged view in section shown in FIG. 5 and operates as follows.

Two backvalves 63,65 are arranged within a recess in the elongate body 41. Valve 63 is of a ball type with a valve seat 67 and a ball 69. The other backvalve 65 is accommodated in an annular space within body 41 and involves an annular valve seat 71 cooperating with a tubular elastic hose piece 73 resting against said valve seat 71 in its neutral position. A side connection 75 provides access to outlet passage 59.

The valve arrangement shown in FIG. 5 cooperates with a pulse generator not shown, said pulse generator imparting to the heating medium pulsating movement whereby via inlet passage 57 ball valve 63 opens on a positive pulse, whereas the other back valve 65 provides connection between outlet passage 59 and inlet passage 57 on a negative pulse. A pulsating system useful for the purpose is disclosed in Swedish patent 9404021-9 in great detail and can be used together with the valve system shown in FIG. 5 to provide for circulation of the heating medium through the balloon for improving heat transfer.

In accordance with the invention it is advantageous to use a material in the bladder which is highly elastic and capable of substantial axial as well as radial extension. It is preferred that the material has an elongation to break of at least more than about 700% and preferably about 1000% or more. A silicon rubber, such as manufactured and sold by Dow Corning, is a suitable material and if axially extended up to say 3 times it can still be radially expanded four to five times. Accordingly, such material can be adapted to a variety of cavity sizes and degrees of extension both axially and radially.

In accordance with one embodiment of the invention the bladder 9 can be preshaped for adaptation to the shape of the uterus cavity in that it widens towards the distal end thereof. In preparation for insertion into the uterus cavity bladder 9 will be axially extended so as to closely surround the catheter tube.

The filling and emptying of the system with regard to the heating medium takes place as follows.

In preparation for treatment the medium is introduced through inlet passage 57 and passes through back valve 63 and over element 61 to reach the interior of bladder 9 through openings 19. In this filling operation the medium displaces air in the system and the air is discharged through outlet passage 59 and a connecting passage 60 as described further below and is replaced by medium.

After concluded heat treatment the medium is drawn from the system via outlet passage 59, through side connection 75, back valve 65 and inlet passage 57 which, in this emptying procedure, acts as a discharge passage.

In FIG. 6 there is shown part of a pulse generating system also including means for introducing heat medium into the system at the same time evacuating air from the system.

Inlet passage 57 and connecting passage 60 are indicated in FIG. 6. When filling the system heating medium is introduced into the system using for example a syringe 79 which via a passage or conduit 81 introduces the medium to pass a pulse generating membrane 83 and further into inlet passage 57. The evacuation of air takes place through outlet passage 59 and connecting passage 60 via a pressure sensing membrane 85, a passage 89, a safety valve 87 and a discharge conduit 91. Membranes 83,85 and safety valve 87 are arranged in a housing 77 which is adapted for connection to a central unit providing the desired functions for the instrument. Such connecting housing 77 and functions provided in connection with the central unit are described more fully in the above-mentioned Swedish patent 9404021-9, the full disclosure of which is introduced herein by reference.

Using the instrument shown in FIGS. 4 and 6 the preparations are the same as described in relation to FIGS. 1 and 2 and before inserting the instrument into the cavity subject to treatment evacuation of air from the instrument, which is important for efficient function, is performed in a simple manner and in one step by injecting heating liquid using syringe 79, said liquid passing through passage 81 via membrane 83 into inlet passage 57 and further through back valve 63 through inlet tube 17 into the bladder 9. Keeping the distal end of the instrument downward air in bladder 9 and other parts of the instrument will be displaced through outlet passage 59, and connecting passage 60, via membrane 85, passage 89, safety valve 87 in open position and discharge conduit 91. When the medium appears at conduit 91 and all air has been removed housing 77 is inserted into its recess in the central unit. This will actuate the safety valve 87 and the balloon is deflated by retracting the syringe piston. The safety valve can, of course, be replaced by an ordinary valve to be closed after the evacuation of air. The instrument is now ready for proper treatment as outlined above.

With reference to FIG. 6 it can be seen that rather than described in Swedish patent 9404021-9 the pressure sensing membrane 85 is positioned in connection with connecting passage 60 and outlet passage 59, which is an advantage since the pressure as measured will better reflect the bladder pressure.

In the introductory part of the specification reference was made to known catheters requiring dilatation to 8–9 mm as a preparation for catheter insertion. The catheter diameter problem will be particularly pronounced in a design where the length of the bladder is varied by the use of a sleeve surrounding the bladder, such as described in WO96/26695.

The present invention makes it possible to significantly reduce the diameter of the part of the catheter to be inserted down to diameters of about 5 to 6 mm. By this reduction of the diameter of the catheter substantial dilatation can be avoided and thereby the requirement for anesthesia will be significantly reduced.

The embodiments described above are all embodying the inventive concept of adapting the length of the bladder to the depth of the cavity subject to treatment, and this concept substantially reduces the risk for excessive heating of the sensitive cervical canal and its cervix at the same time as the instrument can be designed so as to avoid undue dilitation of the cervical canal before insertion of the instrument.

As an alternative to thermal treatment of human uteri the invention also provides a device for thermal treatment of mammalian body cavities or ducts in general, such as for treating a mammalian urethra. Such alternative may involve treatment of prostate disorders. This alternative device contains features described in appended claim 24. The device can incorporate all features contained in the appended dependent device claims.

What is claimed is:

1. A method of thermal treatment of a human uterus cavity lining, comprising the steps:
   a) estimating the depth of said cavity;
   b) adjusting and securing the distance between the axial ends of the heat-emitting part of an elastic bladder to match said cavity depth;

c) inserting the bladder prepared as per step b) above into said cavity;

d) inflating said bladder by introducing a fluid therein under pressure to bring said bladder into contact with substantially all of said lining;

e) heating said fluid to a treatment temperature and maintaining said temperature for a period of time resulting in necrosis of substantially all of said lining; and f) removing said fluid from said bladder and withdrawing the latter in a collapsed state from said cavity.

2. A method according to claim 1, wherein said distance is adjustable between a minimum length matching a minimal cavity depth and a maximum length matching a maximal cavity depth.

3. A method according to claim 2, wherein the distance given by said minimum length results in a prestretched position of the bladder.

4. A method according to claim 1, wherein said fluid is circulated within or through said bladder during treatment.

5. A method according to claim 1, wherein said fluid is heated inside said bladder.

6. A method according to claim 1, wherein said fluid is heated outside said bladder.

7. The method of claim 1, wherein said step of estimating the depth of said cavity further comprises the step of:

using a sound probe to measure the depth of the cavity plus a length of a cervical canal.

8. A method of thermal treatment of a human uterus cavity lining, comprising the steps:

a) estimating the depth of said cavity;

b) inserting an axially extended elastic bladder into said cavity;

c) adjusting and maintaining during treatment the distance between the axial ends of the heat-emitting part of said bladder to match said cavity depth;

d) inflating said bladder by introducing a fluid therein under pressure to bring said bladder into contact with substantially all of said lining;

e) heating said fluid to a treatment temperature and maintaining said temperature for a period of time resulting in necrosis of substantially all of said lining; and f) removing said fluid from said bladder and withdrawing the latter in a collapsed state from said cavity.

9. A method according to claim 8, wherein said distance is adjustable between a minimum length matching a minimal cavity depth and a maximum length matching a maximal cavity depth.

10. The method of claim 8, wherein said step of estimating the depth of said cavity further comprises the step of:

using a sound probe to measure the depth of the cavity plus a length of a cervical canal.

11. A device for carrying out hyperthermia in a mammalian uterus cavity, comprising an elongate, rigid distal section and a flexible and elastic bladder encompassing said distal section which, together with said bladder, is intended for insertion into said uterus cavity, further comprising means for the supply of a heat-transmitting medium under pressure for the expansion of said bladder within said uterus cavity, and heating means for heating said medium, the device further comprising an intermediate section whose distal part when inserted is positioned in a cervix canal belonging to said uterus, and a proximal section for operating the device, said distal and intermediate sections containing at least a central tube, whose distal part is surrounded by said bladder and is provided with at least one outlet for said medium within said bladder, and whose intermediate part is surrounded by an axially displacable tube, onto whose distal end the proximal end of said bladder is attached, characterized by means for determining the axial position of the distal end of said axially displacable tube and thereby also the axial position of the proximal end of said bladder so that the heat-emitting length of said bladder matches the depth of a cavity subject to treatment, and means for locking said tube with its distal end in such matching position.

12. A device according to claim 11, wherein said displacable tube is axially displacable between a first position matching a minimal cavity depth and a second position matching a maximal cavity depth.

13. A device according to claim 12, wherein the distance given by said minimal depth results in a pre-stretched position of the bladder.

14. A device according to claim 11, comprising means generating circulation through said bladder.

15. A device according to claim 11, wherein said heating means is comprised by a heating element placed within said bladder.

16. A device according to claim 11, wherein said heating means is comprised by a heating element placed within said intermediate section.

17. A device according to claim 11, wherein said heating element is selected from elements of the type based on electric resistance heating, microwaves, laser and autocontrol.

18. A device according to claim 17, wherein said auto-control type of element contains PTC or Curie point materials.

19. A device according to claim 11, characterized by a valve arranged at the distal end of said central tube by which air remaining in the system can be evacuated, said tube at its distal end being fixed to the distal wall of the bladder.

20. A device according to claim 11, characterized by an inlet passage for introducing said medium into the bladder, and by an outlet passage for said medium.

21. A device according to claim 20, wherein said outlet passage enables evacuation of air from the system in connection with such introduction of medium.

22. A device according to claim 21, characterized by a pulsating pressure means placed in said inlet passage, and by counteracting back valves placed in said inlet passage between said pulsation means and said bladder, one of said valves opening said inlet passage on a positive pulse, and the other valve opening connection between said outlet passage and said inlet passage on a negative pulse, thereby creating circulation of said medium through said bladder.

23. A device according to claim 20, characterized by a pulsating pressure means placed in said inlet passage, and by counteracting back valves placed in said inlet passage between said pulsation means and said bladder, one of said valves opening said inlet passage on a positive pulse, and the other valve opening connection between said outlet passage and said inlet passage on a negative pulse, thereby creating circulation of said medium through said bladder.

24. A device according to claim 20, characterized by a pressure sensing means connected to said outlet passage for measuring pressure inside the bladder during treatment.

25. A device according to claim 20, characterized by an intermediate tube concentric with and surrounding the central tube, said intermediate tube being connected at its distal end to the distal end of said axially displacable tube so as to move as a unit together with said axially displacable tube, the distal part of said outlet passage being formed by a gap defined between said central tube and the surrounding intermediate tube.

26. A device according to claim 25, wherein said axially displacable tube surrounds the intermediate tube with the formation of an annular gap acting as a thermal insulation to protect the cervical tissue from excessive heating.

27. A device according to claim 11, wherein said axially displacable tube surrounds the central tube with the formation of an annular gap acting as a thermal insulation to protect the cervical tissue from excessive heating.

28. A device for thermal treatment of a mammalian urethra, comprising an elongate, rigid distal section and a flexible and elastic bladder encompassing said distal section which, together with said bladder, is intended for insertion into said urethra, further comprising means for the supply of a heat-transmitting medium under pressure for the expansion of said bladder within said urethra, and heating means for heating said medium, the device further comprising an intermediate section, and a proximal section for operating the device, said distal and intermediate sections containing at least a central tube, whose distal part is surrounded by said bladder and is provided with at least one outlet for said medium within said bladder, and whose intermediate part is surrounded by an axially displacable tube, onto whose distal end the proximal end of said bladder is attached, characterized by means for determining the axial position of the distal end of said axially displacable tube and thereby also the axial position of the proximal end of said bladder so that the heat-emitting length of said bladder matches the area subject to treatment, and means for locking said tube with its distal end in such matching position.

* * * * *